US007635784B2

(12) United States Patent
Cleary et al.

(10) Patent No.: US 7,635,784 B2
(45) Date of Patent: Dec. 22, 2009

(54) PROCESS FOR THE PREPARATION OF 3-AMINO-PENTAN-1,5-DIOL

(75) Inventors: Thomas Cleary, Florence, SC (US); Yaohui Ji, Florence, SC (US); Gary R. Lee, Belmont, CA (US); Thimma Rawalpally, Florence, SC (US); Keshab Sarma, Sunnyvale, CA (US)

(73) Assignees: Hoffmann-La Roche Inc., Nutley, NJ (US); Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/135,240

(22) Filed: Jun. 9, 2008

(65) Prior Publication Data
US 2008/0312467 A1 Dec. 18, 2008

Related U.S. Application Data

(60) Provisional application No. 60/934,864, filed on Jun. 15, 2007.

(51) Int. Cl.
*C07C 269/00* (2006.01)
(52) U.S. Cl. .................................. 560/157; 560/160
(58) Field of Classification Search .................. None
See application file for complete search history.

(56) References Cited

U.S. PATENT DOCUMENTS

2005/0107408 A1  5/2005  Goldstein

2008/0154063 A1* 6/2008 Cain et al. ............. 564/443

FOREIGN PATENT DOCUMENTS

| EP | 1 106 614 | 6/2001 |
|---|---|---|
| WO | WO 01/29401 | 4/2001 |
| WO | WO 02/18379 | 3/2002 |
| WO | WO 02/64594 | 8/2002 |
| WO | WO 2008/068171 | 6/2008 |
| WO | WO 2008/077799 | 7/2008 |

OTHER PUBLICATIONS

Lesma et al, *Jour. of Orgnaic Chem.*, 71 (2006) 3317-3320 XP002504521.
Ohno M et al, *Jour. of the Amer. Chem. Soc.*, 103:9, (1981) 2405-2406 XP001155281.
Adachi, K et al, *Chimia, Aarau, CH*, 40:9 (1986) 311-314 XP002049345.
Liu, Y-S et al *Jour. of Organic Chem.* 63, 3471-3473, (1998) XP00257609.
Tomori et al, *Heterocycles*, 44(1) (1997) 213-225 XP001539296.
Grob et al., Helvetica Chimica Acta, vol. 8, pp. 2145-2155 (1964).
Feuer et al., J. Amer. Chem. Socl. vol. 77 pp. 5427-5428 (1955).
Aycock, D. F. Organic Process Research & Development vol. 11 pp. 156-159 (2007).
Josey et al., J. Org. Chem. vol. 27 pp. 2466-2470 (1962).

* cited by examiner

*Primary Examiner*—Paul A Zucker
(74) *Attorney, Agent, or Firm*—George W. Johnston; Patricia S. Rocha-Tramaloni; Kimberly J. Prior

(57) ABSTRACT

The present invention provides a novel method for preparing a key intermediate, 3-amino-pentan-1,5-diol (2), which is useful for the preparation of 6-(2,4-difluorophenoxy)-2-[3-hydroxy-1-(2-hydroxyethyl)-propylamino]-8-methyl-8H-pyrido[2,3-d]pyrimidine-7-one (1) a MAP-kinase inhibitor useful in the treatment of rheumatoid arthritis.

10 Claims, No Drawings

PROCESS FOR THE PREPARATION OF 3-AMINO-PENTAN-1,5-DIOL

PRIORITY TO RELATED APPLICATIONS

This application claims the benefit of U.S. Provisional Application No. 60/934,864, filed Jun. 15, 2007, which is hereby incorporated by reference in its entirety.

BACKGROUND OF THE INVENTION

Rheumatoid arthritis (RA) is a systemic disease of unknown etiology that occurs predominantly in women. The progressive joint destruction associated with RA is mediated by a complex inflammatory tissue called pannus that is composed of macrophages, fibroblasts, synoviocytes, and blood vessels. Secreted proteins called cytokines control the formation and function of pannus. Specific cytokines that are believed to play a role in mediating the inflammation of RA include TNFα, IL-1β, and IL-6.

P38α MARK is an enzyme important to the intracellular signaling pathway for the generation of TNFα and IL-1b. Multiple extracellular stimuli including stress signals such as lipopolysaccharide, osmotic or heat shock, and pro-inflammatory cytokines such as TNFα, IL-1β stimulate the P38 pathway. Activation of the P38α pathway causes both transcriptional and translation modulation of gene expression of TNFα, IL-1β that is both cell type and signal specific.

Biological agents that selectively neutralize pro-inflammatory cytokines (tumor necrosis factor such as TNFα and interleukin [IL]-1β) have been shown to reduce the number of swollen and tender joints and to retard the destruction of joint tissue. P38 inhibitors of the pyridinylimadazole class block the destruction of joint tissue and the production of the TNFα and IL-1β in monocytes and in animal models of arthritis. Currently, there are no marketed, orally active, safe and effective agents that act primarily to inhibit TNFα or IL-1β. 6-(2, 4-difluorophenoxy)-2-[3-hydroxy-1-(2-hydroxyethyl)-propylamino]-8-methyl-8H-pyrido[2,3-d]pyrimidine-7-one (1) is being developed as an oral agent that will suppress IL-1β, TNFα, and related cytokine production, with the potential to provide increased safety and efficacy compared to the current standard oral therapies for RA.

International patent publications; WO 02/18379 (A2), WO 01/29401 (A1), and WO 02/064594 (A2) and U.S. Patent Application Publication 2005/0107408 (A1) disclose methods for the preparation of 6-(2,4-difluorophenoxy)-2-[3-hydroxy-1-(2-hydroxyethyl)-propylamino]-8-methyl-8H-pyrido[2,3-d]pyrimidine-7-one (1) and its use for the treatment of P38 mediated disorders.

6-(2,4-difluorophenoxy)-2-[3-hydroxy-1-(2-hydroxyethyl)-propylamino]-8-methyl-8H-pyrido[2,3-d]pyrimidine-7-one (1) can be prepared by coupling 3-amino-pentan-1,5-diol (2) and a sulfone intermediate (3) as shown below in Scheme 1:

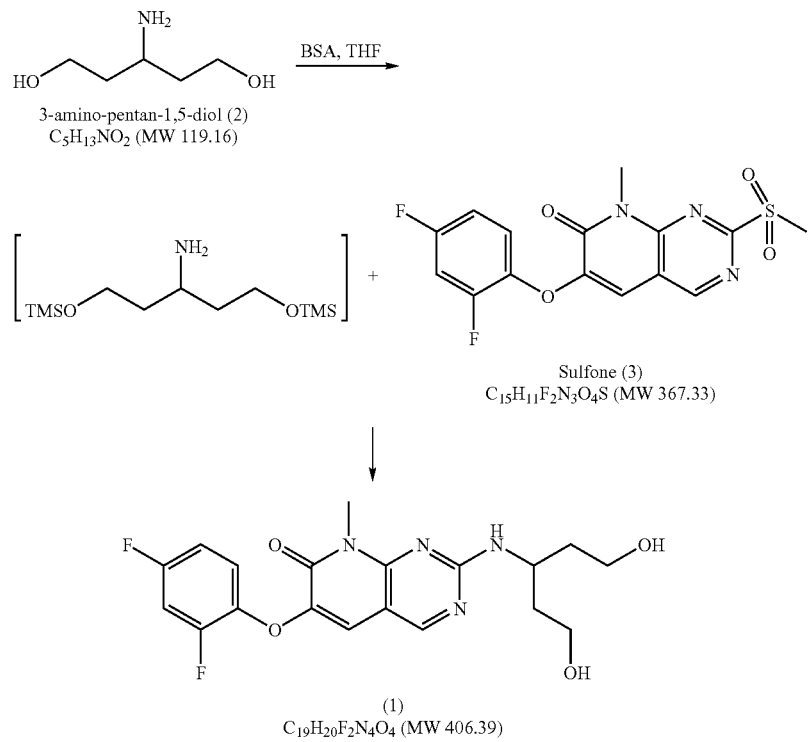

One of the key intermediates for preparing compound (1) is 3-amino-pentan-1,5-diol (2). Several synthetic routes for preparing intermediate (2) have been disclosed in the literature (Helvetica Chimica Acta, vol. 8, page 2145-2155 (1964), and in copending U.S. Provisional Patent Application No. 60/876,828. These synthetic routes have the shortcomings of high manufacturing costs, environmental impact, and technical difficulties for commercial scale manufacturing.

In the literature method (Helvetica Chimica Acta, vol. 8, page 2145-2155 (1964)) the 3-amino-pentan-1,5-diol (2) (shown in Scheme 2) is prepared via the lithium aluminum hydride (LAH) reduction of unprotected diethyl-3-amino-glutarate HCl salt (4).

Scheme 2

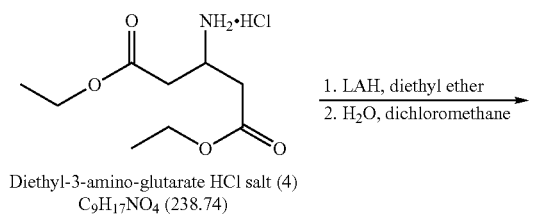

Diethyl-3-amino-glutarate HCl salt (4)
$C_9H_{17}NO_4$ (238.74)

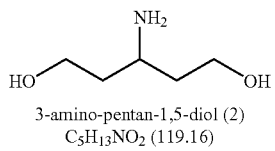

3-amino-pentan-1,5-diol (2)
$C_5H_{13}NO_2$ (119.16)

The diethyl-3-amino-glutarate HCl salt (4) is prepared following the literature procedure (J. Amer. Chem. Soc. vol. 77, page 5427 (1955)). The isolation of the water soluble 3-amino-pentan-1,5-diol (2) from the aluminum salts is very difficult and results in poor yields. Handling LAH on a large scale is hazardous.

Another process for the production of 3-amino-pentan-1,5-diol (2) is described in U.S. Provisional Patent Application No. 60/876,828 and shown in Scheme 3.

Scheme 3

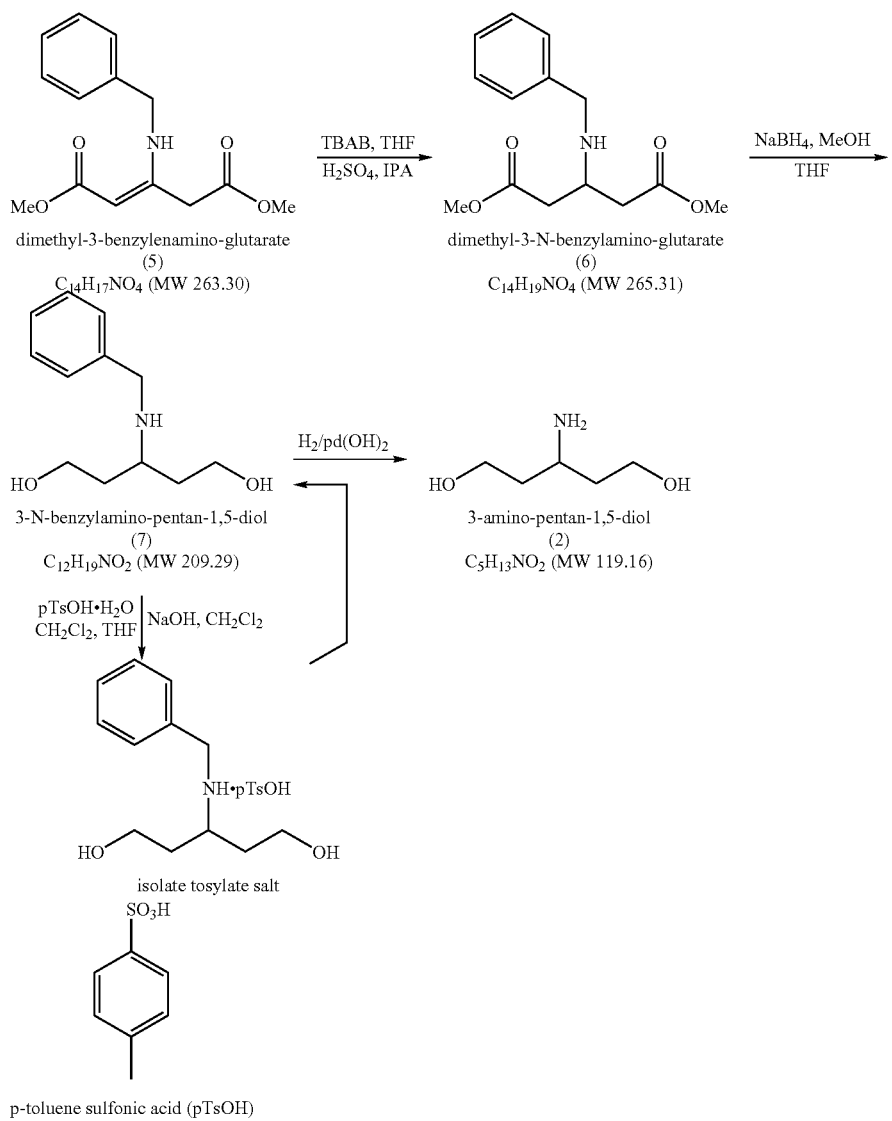

Reduction of de-benzylated dimethyl-3-N-benzylamino-glutarate (6) followed by aqueous workup results in poor recovery of 3-amino-pentan-1,5-diol (2). Very good recovery of 3-N-benzylamino-petan-1,5-diol (7) achieved from the aqueous workup after the reduction of dimethyl-3-N-benzy-lamino-glutarate (6). The 3-N-benzylamino-petan-1,5-diol (7) is not soluble in water hence the extraction from the aluminum salts is quite facile. The 3-N-benzylamino-petan-1,5-diol (7) is purified via crystalline tosylate salt. The final deprotection of the benzyl group to obtain 3-amino-pentan-1,5-diol (2) was possible under non-aqueous condition.

Reduction of the dimethyl-3-N-benzylamino-glutarate (6) to the 3-N-benzylamino-petan-1,5-diol (7) can be accomplished in two methods. One method employs sodium borohydride, which is inexpensive. This method requires a long reaction time, e.g. 72 hours, and results in an impurity that is difficult to remove from the down stream process. An alternative method employs a toluene solution of sodium bis(2-methoxyethoxy)aluminum hydride (vitride), an easily scalable reducing agent. The recovery of the benzyl protected 3-N-benzyl-amino-pentane-1,5-diol (7) from the aluminum salts after vitride reduction requires multiple, e.g. five or six, extractions with dichloromethane solvent. Formation of a crystalline tosylate salt of the aminodiol eliminates the need for distillation. This process, starting from dimethyl-3-N-benzylamino-glutarate (6), has an overall yield of 69%.

SUMMARY OF THE INVENTION

The present invention provides a novel method for preparing a key intermediate, 3-amino-pentan-1,5-diol (2), which is useful for the preparation of 6-(2,4-difluorophenoxy)-2-[3-hydroxy-1-(2-hydroxyethyl)-propylamino]-8-methyl-8H-pyrido[2,3-d]pyrimidine-7-one (1) that is being investigated as a MAP-kinase inhibitor for use in the treatment of rheumatoid arthritis.

The 3-amino-pentan-1,5-diol (2) is synthesized in two isolated steps (four chemical reactions) starting from readily available inexpensive dimethylacetone-1,3-dicarboxylate (8). The key reactions are the reduction of dimethyl-3-amino-N-Boc-glutarate (10) (tert-butoxycarbonyl=Boc) using sodium borohydride (Boc protecting group accelerates the rate of ester reduction significantly) and the combined deprotection of the Boc group and purification of the 3-amino-pentan-1,5-diol (2) with one single chemical operation using acidic resin. The Amberlyst polymer based ion exchange resin involves mostly the use of functionalized styrene divinylbenzene copolymer with different surface properties and porosities. The functional group is generally of the sulphuric acid type. These resins are supplied as gellular or macroreticular spherical beads. Examples of commercial acidic resin are Amberlite IR-120, Amberlyst 15, Amberlite FPC22H, and AmberliteFPC23H.

The use of the acidic resin eliminates the need for an aqueous workup in the last step and provides 3-amino-pentan-1,5-diol (2) in high yield and good quality. The overall yield starting from dimethylacetone-1,3-dicarboxylate (8) is 89%, and the purity of the 3-amino-pentan-1,5-diol (2) is 99.5%.

DETAILED DESCRIPTION OF THE INVENTION

The present invention provides a straight forward two-step process for the preparation of 3-amino-pentan-1,5-diol from an inexpensive, readily available starting material, dimethylacetone-1,3-dicarboxylate (8). The process of the invention further provides for the facile reduction of the dimethyl-3-amino-N-Boc-glutarate (10) with a safe and inexpensive reducing agent, such as sodium borohydride. The process of the invention can be depicted by Scheme 4:

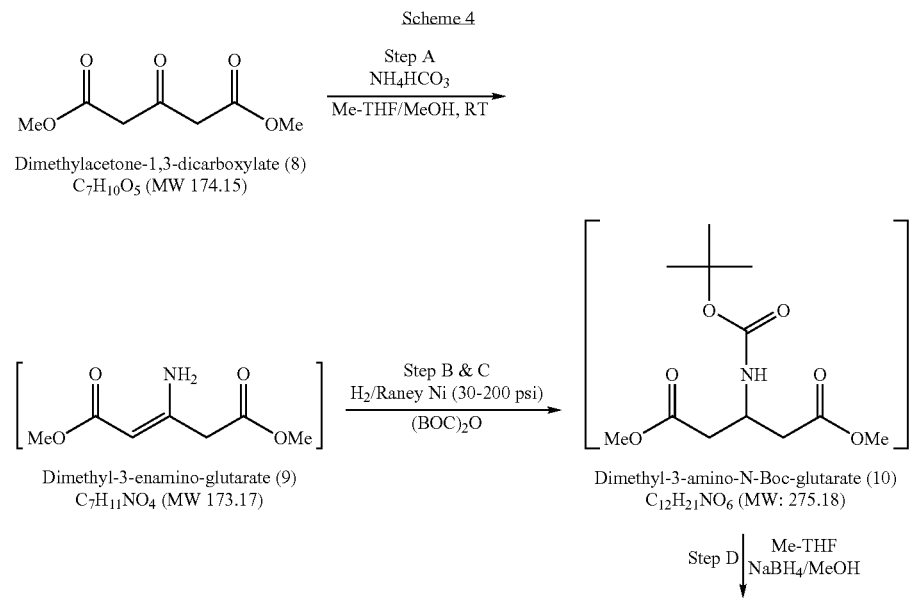

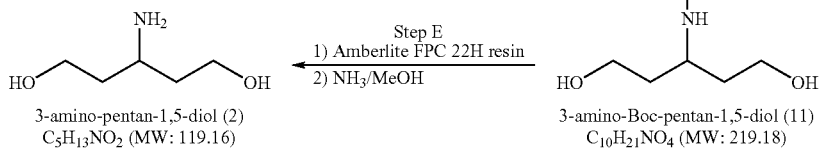

3-amino-pentan-1,5-diol (2)
C₅H₁₃NO₂ (MW: 119.16)

Step E
1) Amberlite FPC 22H resin
2) NH₃/MeOH

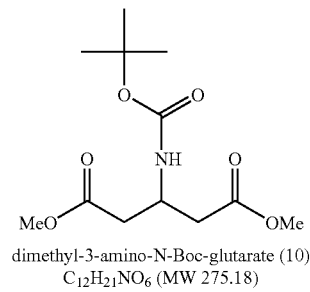

3-amino-Boc-pentan-1,5-diol (11)
C₁₀H₂₁NO₄ (MW: 219.18)

The intermediate dimethyl-3-amino-N-Boc-glutarate (10) can be prepared in two steps starting from inexpensive dimethylacetone-1,3-dicarboxylate (8) in accordance with Scheme 5. First, the intermediate dimethyl-3-enamino-glutarate (9) is obtained by treating the dimethylacetone-1,3-dicarboxylate (8) with ammonium hydrogen carbonate in MeOH or Me-THF solvents (Step A). 2-Methyltertrahydrofuran (Me-THF) is an aprotic ether solvent that, while being a strong Lewis base like THF, is only partially miscible with water. Me-THF is a commercially available solvent that is produced from renewable resources. The properties of Me-THF place it between tetrahydrofuran and diethyl ether in solvent polarity and Lewis base strength (Organic Process Research & Development Vol. 11, page 156 (2007).

-continued dimethyl-3-amino-N-Boc-glutarate (10)
C₁₂H₂₁NO₆ (MW 275.18)

The intermediate dimethyl-3-amino-N-Boc-glutarate (10) can be reduced with sodium borohydride to 3-amino-N-Boc-pentan-1,5-diol (11), which is then isolated after aqueous workup (Step D).

Scheme 5

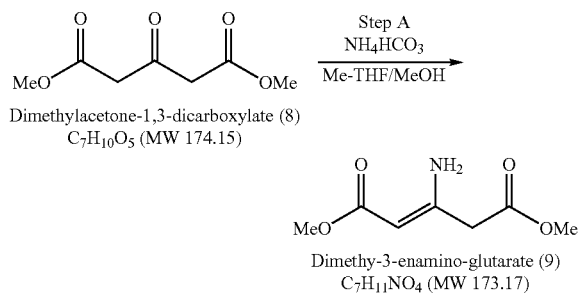

Dimethylacetone-1,3-dicarboxylate (8)
C₇H₁₀O₅ (MW 174.15)

Dimethy-3-enamino-glutarate (9)
C₇H₁₁NO₄ (MW 173.17)

A one-pot reduction of dimethyl-3-enamino-glutarate (9) followed by protection of the free amine can be achieved using Raney hydrogenation and di-tert-butyldicarbonate in MeOH or Me-THF solvents (Step B/C)

Step B/C

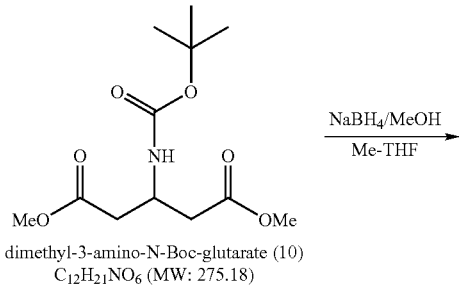

Step D

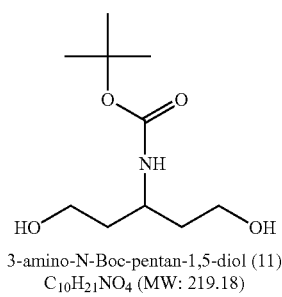

dimethyl-3-amino-N-Boc-glutarate (10)
C₁₂H₂₁NO₆ (MW: 275.18)

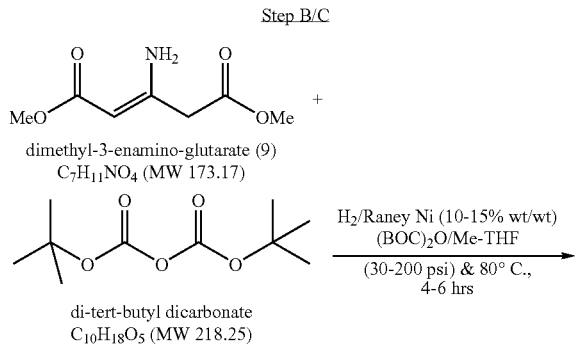

3-amino-N-Boc-pentan-1,5-diol (11)
C₁₀H₂₁NO₄ (MW: 219.18)

Finally, deprotection of the N-tert-butoxycarbonyl group and purification of the desired 3-amino-pentan-1,5-diol (2) is possible by refluxing the 3-amino-N-Boc-pentan-1,5-diol (11) with a strong acidic resin, and the desired aminodiol (2)

is released from the resin by treating the resin with 7N aqueous ammonium hydroxide solution (Step E).

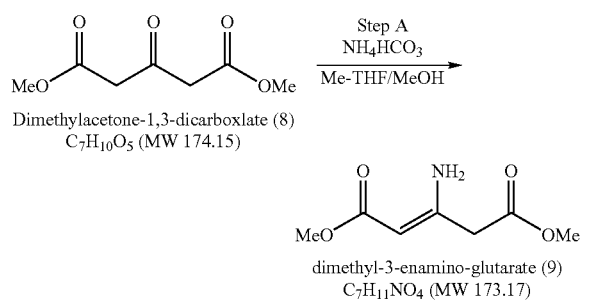

3-amino-N-Boc-pentan-1,5-diol (11)
$C_{10}H_{21}NO_4$ (MW: 219.18)

Amberlite FPC22H
Me-THF,
75° C.
3-4 hours $NH_3$ in MeOH
4° C. to RT 3-amino-pentan-1,5-diol (2)
$C_5H_{13}NO_2$ (MW: 119.16)

EXAMPLES

In accordance with the present invention, the following examples are provided to illustrate preparation of the key intermediate (2), which is useful for the preparation of 6-(2,4-difluorophenoxy)-2-[3-hydroxy-1-(2-hydroxyethyl)-propylamino]-8-methyl-8H-pyrido[2,3-d]pyrimidine-7-one (1).

Example 1

Reaction of dimethylacetone-1,3-dicarboxylate (8) with ammonium bicarbonate (Step A)

Dimethylacetone-1,3-dicarboxlate (8)
$C_7H_{10}O_5$ (MW 174.15)

Step A
$NH_4HCO_3$
Me-THF/MeOH dimethyl-3-enamino-glutarate (9)
$C_7H_{11}NO_4$ (MW 173.17)

A 2 L, four-necked, round bottom flask, equipped with a mechanical stirrer, thermocouple and nitrogen inlet/bubbler was charged with 60 ml of Me-THF, 73.6 g of ammonium hydrogen carbonate, and 80.0 g of dimethylacetone-1,3-dicarboxylate (8) in 180 ml of MeOH. The reaction was stirred at 20° C. for 18 hrs. The progress of the reaction was monitored by gas chromatography. At the end of reaction completion (<1% starting material), the solids were filtered, MeOH was distilled at atmospheric pressure, and the step A product (9) (dimethyl-3-enamino-glutarate) in Me-THF was directly taken into next step (B/C). The gas chromatography showed 98% of (9).

Example 2

Raney Ni Reduction of enamino-diester (9) Followed by Protection with di-tert-butyl dicarbonate (Step B/C)

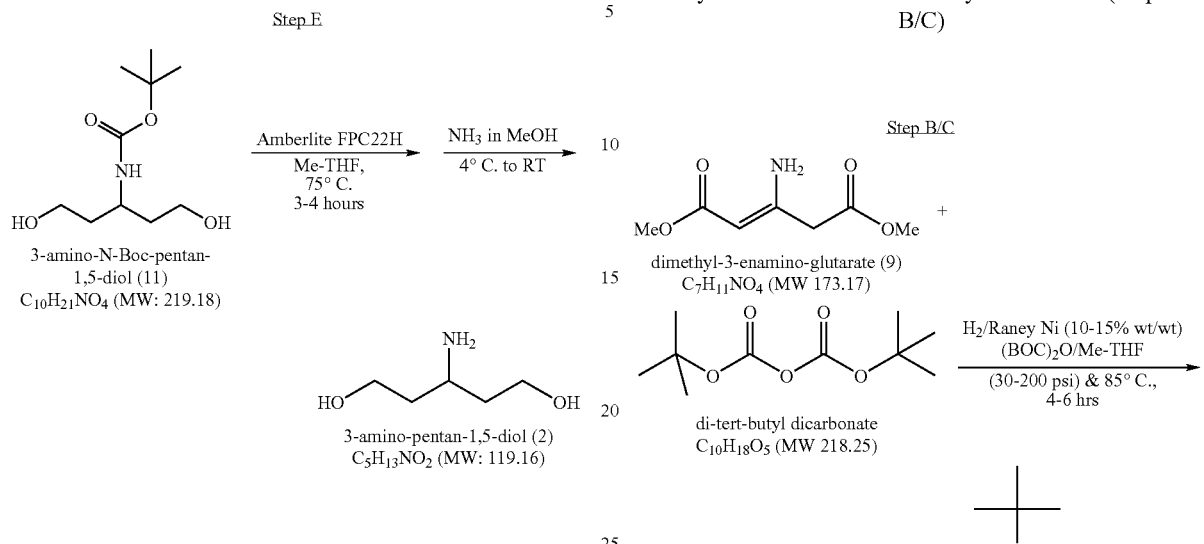

A 1 L autoclave, equipped with a mechanical stirrer, thermocouple, nitrogen, and hydrogen inlet was charged with 220 ml of Me-THF solution containing 80 g of dimethyl-3-enamino-glutarate (9), 96.0 g of di-tert-butyl dicarbonate [$Boc_2O$, 1.1 equiv] dissolved in 120.0 ml of Me-THF, and 8.0 g of sponge Raney Nickel. The reaction mixture was stirred and then the reactor was placed under vacuum and held for 5 minutes. The reactor then was pressurized to 20 psi nitrogen and held for 5 minutes. The vacuum/nitrogen cycle was repeated three more times. The reaction was left under vacuum. The reaction was pressurized between 20-100 psi hydrogen and held for 5 minutes, followed by release of hydrogen to 10 psi pressure. The hydrogen purge was repeated three more times. The reaction was then left between 20-100 psi hydrogen pressure, and the reaction was heated. When the reaction temperature reached 85° C., the $H_2$ pressure was adjusted between 30-200 psi and the reaction was stirred at a rate of 500 rpm. The reaction was held at 85° C./between 30-200 psi $H_2$. If you are running the reaction at 30 psi $H_2$ pressure the reaction requires degassing one time with hydrogen after 3 hrs. After 6 hrs the batch was cooled to a temperature of 40° C. and $H_2$ pressure was released. The reaction product was sampled and the reaction monitored by gas chromatography (<1% starting material). The reaction was cooled to 20° C., filtered through celite, and the organic filtrate collected. The organic layer containing the desired dimethyl-3-amino-N-Boc-glutarate (10) was directly carried forward into the next step.

Example 3

Sodium borohydride Reduction of dimethyl-3-amino-N-Boc-glutarate (10) and Formation of 3-amino-N-Boc-pentan-1,5-diol (11)

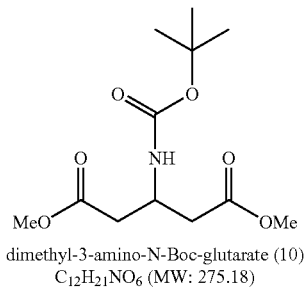

dimethyl-3-amino-N-Boc-glutarate (10)
$C_{12}H_{21}NO_6$ (MW: 275.18)

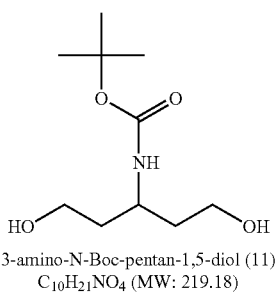

3-amino-N-Boc-pentan-1,5-diol (11)
$C_{10}H_{21}NO_4$ (MW: 219.18)

A 2 L, four-necked, round bottom flask, equipped with a mechanical stirrer, thermocouple, addition funnel and nitrogen inlet/bubbler was charged with 117.6 g dimethyl-3-amino-N-Boc-glutarate (10) in Me-THF solution (34 wt % in Me-THF) and with 16.5 g of sodium borohydride. After heating to 55° C., 26.7 ml of anhydrous Methanol diluted with 100 ml Me-THF was slowly added to the reaction. The reaction temperature was maintained between 55° C. and 60° C. throughout the addition. After the addition, the batch was held at a temperature of 55° C. The process of the reaction was monitored by NMR. The reaction was complete in 3 hrs (<0.5% of SM) based on the NMR. The excess borane was quenched with 20 ml of acetone. The batch was reverse quenched into a vessel containing 125 ml of water at 60° C., followed by addition of 30 ml of 3N HCl over a period of 1 hour. During acid addition, the reaction pH went down from 14 to 11. The organic phase containing the desired 3-amino-N-Boc-pentan-1,5-diol (11) was separated at 60° C. and directly taken into the next deprotection and purification step.

Example 4

Deprotection and Purification of 3-amino-N-Boc-pentan-1,5-diol (11) and the Formation of 3-amino-pentan-1,5-diol (2)

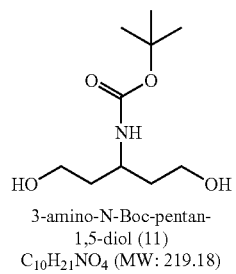

3-amino-N-Boc-pentan-1,5-diol (11)
$C_{10}H_{21}NO_4$ (MW: 219.18)

-continued

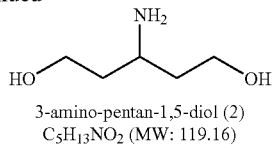

3-amino-pentan-1,5-diol (2)
$C_5H_{13}NO_2$ (MW: 119.16)

A 1 L, four-necked, round bottom flask, equipped with a mechanical stirrer, thermocouple, addition funnel and nitrogen inlet/bubbler was charged with 150.0 ml of 3-amino-N-Boc-pentan-1,5-diol (11) solution and 96.0 g of Amberlite FPC22H ion exchange resin. The reaction was heated to 75° C. (batch temp), and the reaction was held at 75° C. The progress of the reaction was monitored by Gas chromatography (GC). The deprotection was complete in 4 hrs (<1% SM) based of GC. The batch was cooled down to 20° C. and filtered to collect the resin. The resin was rinsed with 50 ml of methanol. The resin was transferred to a separate 1 L reactor, which was charged with pre-cooled (4° C.) 150 ml of 7N ammonia methanol solution [made from bubbling ammonia into methanol at 0° C.]. The addition was exothermic; and therefore, the methanolic ammonia was added very slowly to the resin. The reaction was warmed to room temperature (RT), and the reaction was held at 20° C. for an hour. The batch was filtered, with the resin and the methanolic ammonia solution containing the desired compound collected separately. The resin extraction process was repeated with methanolic ammonia twice using 150 ml of 7N ammonia methanol solution. To remove light yellow color, the combined methanolic solution was filtered through a bed of carbon/celite (30 grams of carbon: one inch bed over celite). The methanol was distilled at atmospheric pressure to obtain the desired 3-amino-pentan-1,5-diol (2) in 89% overall yield.

We claim:

1. A one-pot process for preparing dimethyl-3-amino-N-Boc-glutarate (10).

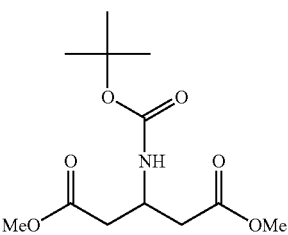

comprising
a) Raney Nickel reduction of a compound of formula (9)

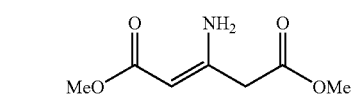

in MeOH or Me-THF; and b) In-situ protection of the amine intermediate with di-tert-butyl dicarbonate in MeOH or Me-THF solvent to form the compound of formula (10)

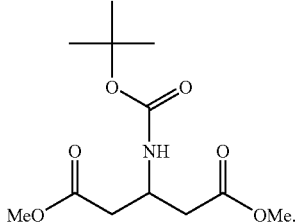

2. The process of claim 1, wherein the compound of formula (9)

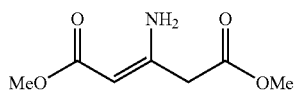

is prepared by the process comprising treating a compound of formula (8)

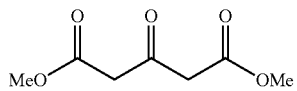

with ammonium hydrogen carbonate in MeOH or Me-THF.

3. A process for preparing a compound of formula (11)

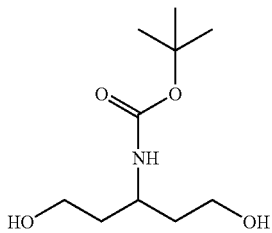

via sodium borohydride reduction of a compound of formula (10)

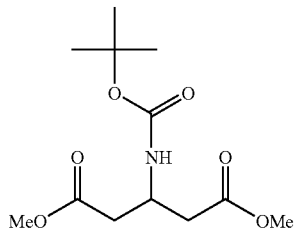

in THF or Me-THF solvents.

4. The process of claim 3, wherein the compound of formula (10)

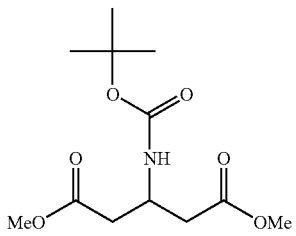

is prepared by the process comprising
a) Raney Nickel reduction of a compound of formula (9)

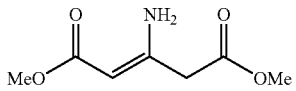

in MeOH or Me-THF; and
b) In-situ protection of the amine intermediate with di-tert-butyl dicarbonate in MeOH or Me-THF solvent to form the compound of formula (10)

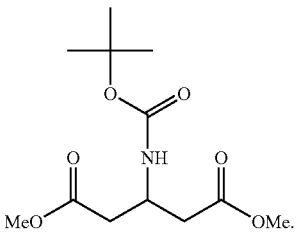

5. The process of claim 4, wherein the compound of formula (9)

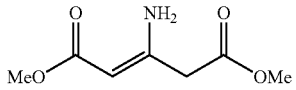

is prepared by the process comprising treating a compound of formula (8)

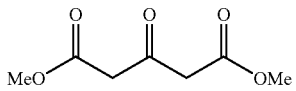

with ammonium hydrogen carbonate in MeOH or Me-THF.

6. A process for the preparation of a compound of formula (2)

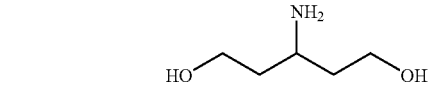

Comprising
   a) Deprotection of the tert-butoxycarbonyl group from a compound of formula (11)

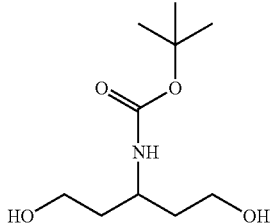

by refluxing with an acidic resin to yield the 3-amino-pentan-1,5-diol formula (2), wherein the amino-diol is bound to the resin; and
   b) In-situ purification of the compound of formula (2) by cleaning the resin with MeOH and releasing the resin bound 3-amino-pentan-1,5-diol (2) by treating the resin with 7N aqueous ammonia hydroxide solution in MeOH.

7. The process of claim 6, wherein the acidic resin is selected from the group consisting of Amberlite IR-120, Amberlyst 15, Amberlite FPC22H, and AmberliteFPC23H.

8. The process of claim 6, wherein the compound of formula (11)

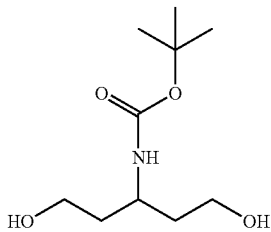

is prepared via sodium borohydride reduction of a compound of formula (10)

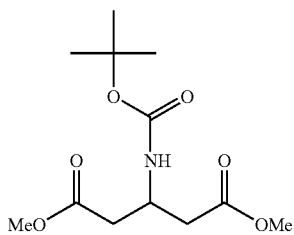

in THF or Me-THF solvents.

9. The process of claim 8, wherein the compound of formula (10)

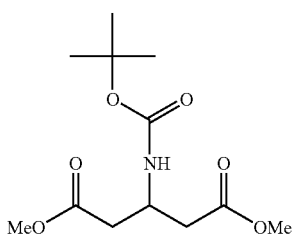

is prepared by the process comprising
   a) Raney Nickel reduction of a compound of formula (9)

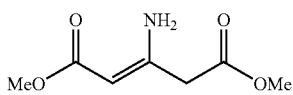

in MeOH or Me-THF; and
   b) In-situ protection of the amine intermediate with di-tert-butyl dicarbonate in MeOH or Me-THF solvent to form the compound of formula (10)

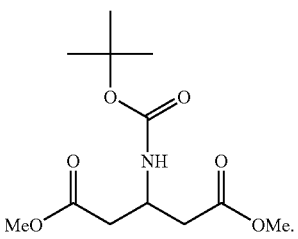

10. The process of claim 9, wherein the compound of formula (9)

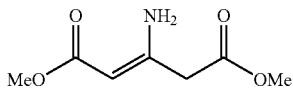

is prepared by the process comprising treating a compound of formula (8)

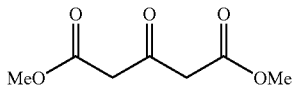

with ammonium hydrogen carbonate in MeOH or Me-THF.

* * * * *